United States Patent [19]

Feichtmayr et al.

[11] 4,336,201
[45] Jun. 22, 1982

[54] PREPARATION OF ELECTRICALLY CONDUCTIVE CAROTENOIDS

[75] Inventors: Franz Feichtmayr, Ludwigshafen; Herbert Naarmann, Wattenheim; Joachim Paust, Neuhofen; Klaus Penzien, Frankenthal, all of Fed. Rep. of Germany

[73] Assignee: BASF Aktiengesellschaft, Ludwigshafen, Fed. Rep. of Germany

[21] Appl. No.: 203,598

[22] Filed: Nov. 3, 1980

[30] Foreign Application Priority Data

Nov. 28, 1979 [DE] Fed. Rep. of Germany ....... 2947797

[51] Int. Cl.$^3$ .................... C07C 175/00; C11C 3/02
[52] U.S. Cl. .............................. 260/410.9 V; 525/326; 525/340; 525/344; 525/353; 525/355; 525/359.4; 525/360; 525/367; 525/377; 560/205; 568/329; 568/343; 568/346; 568/347; 585/351; 549/547
[58] Field of Search ............... 585/351; 525/326, 340, 525/344, 353, 359.4, 355, 360, 367, 377; 260/348.11, 346.11, 410.9 V; 560/205; 568/329, 343, 446, 447

[56] References Cited

PUBLICATIONS

Carotenoids by Karrer et al., Elsevier Pub. Co. Inc., 1950, pp. 6-7.

*Primary Examiner*—William F. Hamrock
*Attorney, Agent, or Firm*—John H. Shurtleff

[57] ABSTRACT

A process for the preparation of an electrically conductive polyene, wherein a polyene which contains one or more chain members of the formula

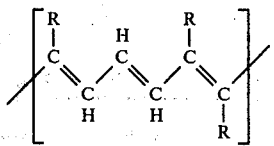

where R is hydrogen or methyl, and which contains a total of not less than seven aliphatic double bonds, is treated, in the absence of moisture and of oxygen, with a strong Lewis acid having a $pk_a$ of from $-10$ to $+4$, or with an alkali metal.

8 Claims, No Drawings

PREPARATION OF ELECTRICALLY CONDUCTIVE CAROTENOIDS

The invention relates to a process for the preparation of electrically conductive polyenes and their use in the electrical industry for the production of solar cells, for the conversion of radiation, for the production of electrical and magnetic switches, and for the antistatic treatment of plastics.

Ber. Bunsenges. Phys. Chem. 83 (1979), 427 discloses that polyaromatics, eg. polyphenylenes, are electrically conductive.

Since there is a need for organic compounds having a sufficiently high conductivity for industrial purposes, it is an object of the present invention to provide such novel conductive organic systems.

We have found that this object is achieved by a process wherein a polyene which contains one or more chain members of the formula

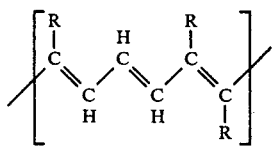

where R is hydrogen or methyl, and which contains a total of not less than seven aliphatic double bonds, is treated, in the absence of moisture and of oxygen, with from 0.03 to 0.9 mole percent, based on polyene employed, of a strong Lewis acid having a $pk_a$ of from $-10$ to $+4$ or of an alkali metal.

The polyenes used according to the invention contain one or more chain members of the above formula where R is hydrogen or methyl, and contain a total of not less than seven, preferably from 11 to 20, aliphatic double bonds. They may additionally contain aliphatic, cycloaliphatic or aromatic radicals. As substituents, the polyenes may contain hydroxyl groups, ether groups, eg. $H_3CO$-groups, aldehyde groups, keto groups, carboxyl groups, carboxylic acid ester groups, chlorine atoms, sulfone groups or triphenylphosphine groups. The said radicals and substituents are preferably at the ends of the polyene chains.

Specific examples of suitable polyenes are: β-carotene, crocetindial, canthaxanthene, sarcinene, sarcinaxanthene, rhodoxanthene, 1,2,1',2'-tetrahydrolycopene, 7,8,11,12-tetrahydrolycopene, 7,8,7',8'-tetrahydrolycopene, 1,2,7,8,11,12-hexahydrolycopene, 1,2,1',2'-tetrahydroneurosporene, 7,8,1',2',7',8'-hexahydrolycopene, phytofluene, 1,2-dihydrophytofluene, phytoene, 6',7'-didehydro-5,6,5',6'-tetrahydro-β,β-carotene-3,5,6,3',5'-pentol, 1-methoxy-1',2'-dihydro-3',4'-dehydro-γ-carotene, anhydrorhodovibrin, 3,4-dihydroanhydrorhodovibrin, spheroidene, cryptoxanthene-5,8,5',8' diepoxide, auroxanthene, torularhodinaldehyde, 3,4-dehydrolycopen-16-al, 3-hydroxy-3'-keto-retrodehydrocarotene, 5,6,5',6'-tetrahydrocanthaxanthene, β,α-carotene-3',6'-dione, (3S,5R,3'S,5'R)-3,3'-dihydroxy-α,α-carotene-6,6'-dione, 7,8,7',8'-tetrahydrocapsorubin, phillipsiaxanthene, 2,2'-diketospirilloxanthene, 1,1'-dimethoxy-1,2,1',2'-tetrahydro-ψ,ψ-carotene-4,4'-dione, 5-hydroxy-4',5'-didehydro-4,5-dihydro-4,5'-retro-β,β-carotene-3,3'-dione, capsorubindione, torularhodine, torularhodine methyl ester, methyl 1'-methoxy-4'-oxo-1',2'-dihydro-χ,ψ-carotene-16(or -17 or -18)-carboxylate, semi-β-carotenone, semi-α-carotenone, 3-hydroxysemi-β-carotenone, 5,6,5',6'-diseco-β,β-carotene-5,6,5',6'-tetrone, 2-(4-hydroxy-3-methyl-but-2-enyl)-β,β-carotene, 7',8',11',12'-dehydrononaprenoxanthene, 11',12'-dehydrononaprenoxanthene, 2,2'-bis-(3-methyl-but-2-enyl)-ε,ε-carotene, deshydroxydecaprenoxanthene, sarcinaxanthene, (2R,6S,2'R,6'S)-2,2'-bis-(4-hydroxy-3-methyl-but-2-enyl)-γ,γ-carotene, 2-[4-(β-D-glucopyranosyloxy)-3-methyl-but-2-enyl]-2'-(4-hydroxy-3-methyl-but-2-enyl)-ε,ε-carotene, 2,2'-bis-[4-(β-D-glucopyranosyloxy)-3-methyl-but-2-enyl]-ε,ε-carotene, 7,8(or 7',8')-dihydrodecaprenoxanthene monoglucoside, 2-(4-hydroxy-3-methyl-but-2-enyl)-2-(3-methyl-but-2-enyl)-3',4'-didehydro-1',2'-dihydro-ε,χ-caroten-1'-ol and tris-anhydrobacterioruberin.

The said starting materials, with their formulae, are described, for example, in O. Straub: "Key to Carotenoids", Birkenhauser Verlag 1976, under numbers 24 to 32, 96 to 99, 140 to 142, 192 to 194 and 205 to 227.

Other suitable starting materials are the polyenes described in Angew. Chemie 89 (1977), 198, which are referred to as macrolides and which possess a sugar residue with several, preferably 5 or 6, hydroxyl groups. Polyenes without methyl branches, such as the flexirubin dimethyl ester described in Angew.Chem., loc. cit., may also be used.

According to the invention, the polyenes are converted to the conductive materials by treatment with a Lewis acid or an alkali metal. Examples of suitable Lewis acids having a $pk_a$ of from $-10$ to $+4$ are $AsF_5$, $SbF_5$, $HClO_4$, trifluoroacetic acid, $FSO_3H$, $AgClO_4$, $NO^+SbF_6^-$, $NO_2^+SbF_6^-$, $NO^+AsF_6^-$, $NO^+PF_6^-$, $NO_2^+PF_6^-$, $NO^+BF_4^-$, $NO_2^+BF_4^-$, $NO^+ClO_4^-$, $(CF_3)_2SO_4$, 2,4,6-trinitrophenol, 2,4,6-trinitrophenylsulfonic acid and 2,4,6-trinitrophenylcarboxylic acid.

Examples of suitable alkali metals are sodium and potassium, which may also be employed in the form of a solution, for example in naphthalene or in α-methylstyrene.

The treatment of the polyene with the Lewis acid or the alkali metal is carried out at from $-70°$ to $150°$ C., preferably at from $-10°$ to $100°$ C., especially at from $0°$ to $30°$ C. The acid or alkali metal which complexes with the polyene to give the conductive compound is employed in an amount of from 0.03 to 0.9, preferably from 0.1 to 0.5, mole %, based on polyene.

The additives are incorporated in the absence of moisture (ie. water) and of oxygen (ie. air), and the process is therefore preferably carried out under a noble gas, eg. argon. Non-aqueous solvents which, under the conditions of the process, do not react with the Lewis acid or the alkali metal, may be used as auxiliaries; examples are methylene chloride, tetrahydrofuran, dimethoxyglycol, nitromethane, naphthalene and α-methylstyrene. The electrically conductive polyenes, most of which are deeply colored, are formed, by the novel process, in from a few seconds to a few minutes. Any solvent used is advantageously removed under reduced pressure at below $100°$ C.

The novel process gives highly conductive polyenes. For example, the conductivity of canthaxanthene is increased from $1.4 \times 10^{-10}$ S/cm to $5.1 \times 10^{-4}$ S/cm. The electrical conductivities are measured in S/cm, at $30°$ C., using the method of F. Beck, Berichte Bunsengesellschaft, Physikalische Chemie 68 (1964), 558-567.

The electrically conductive polyenes obtained according to the invention may be used for the antistatic treatment of plastics, for the production of solar cells, for the conversion of radiation, and for the production of electrical and magnetic switches.

In the Examples which follow, parts are by weight.

EXAMPLES 1 TO 10

50 parts of a 10% strength solution (ie. 0.03 mole %) of $SbF_5$ in methylene chloride are added to 10 parts of β-carotene under argon at room temperature in the absence of moisture and of atmospheric oxygen. Complex formation occurs immediately. The solvent is stripped off under reduced pressure and a deep bluish black crystalline compound is obtained, which, on measurement in a conductivity cell, proves to have a conductivity of $3.6 \times 10^{-6}$ S/cm. The conductivity of the β-carotene employed was $3.6 \times 10^{-10}$ S/cm.

Following the procedure described in Example 1, with the polymers and additives shown in the Table, the polyenes having the conductivity shown in the Table are obtained.

TABLE

| Example | Polyene Type and amount | Initial conductivity at 25° C. [S/cm] | Doping agent amount [parts] and type | Conductivity after doping at 25° C. [S/cm] |
|---|---|---|---|---|
| 2 | Crocetindial 10 parts | $1.0 \times 10^{-10}$ | 17 $SbF_5$ about 0.1 mole % | $1.24 \times 10^{-7}$ |
| 3 | Canthaxanthene 10 parts | $1.4 \times 10^{-10}$ | 18 $SbF_5$ about 0.1 mole % | $5.1 \times 10^{-4}$ |
| 4 | Canthaxanthene 10 parts | $1.4 \times 10^{-10}$ | 19.5 $NO^+SbF_6^-$ about 0.1 mole % | $7.8 \times 10^{-4}$ |
| 5 | Canthaxanthene 10 parts | $1.4 \times 10^{-10}$ | 21 $NO_2^+SbF_6^-$ about 0.1 mole % | $9.2 \times 10^{-4}$ |
| 6 | Canthaxanthene 10 parts | $1.4 \times 10^{-10}$ | 6 K about 0.2 mole % | $3.4 \times 10^{-3}$ |
| 7 | Flexirubin dimethyl ester 10 parts | $3.5 \times 10^{-10}$ | 20 $7.2 \times 10^{-2}$ about 0.2 mole % | |
| 8 | Sarcinaxanthene 10 parts | $2.4 \times 10^{-10}$ | 22 $CF_3COOH$ about 0.25 mole % | $3.9 \times 10^{-3}$ |
| 9 | Sarcinene 10 parts | $1.0 \times 10^{-10}$ a | 21 $SbF_5$ about 0.2 mole % | $4.8 \times 10^{-4}$ |
| 10 | Rhodoxanthene 10 parts | $1.0 \times 10^{-10}$ | 15.5 $FSO_3H$ about 0.2 mole % | $6.8 \times 10^{-3}$ |

We claim:

1. A process for the preparation of an electrically conductive polyene which comprises treating a carotenoid having one or more chain members of the formula $$\left[ \begin{array}{c} R \\ | \\ C \\ / \\ \end{array} = \begin{array}{c} H \\ | \\ C \\ \end{array} \begin{array}{c} \\ \\ C \\ / \\ H \end{array} = \begin{array}{c} \\ \\ C \\ \\ H \end{array} \begin{array}{c} R \\ | \\ C \\ / \\ \end{array} = \begin{array}{c} \\ \\ C \\ \\ | \\ R \end{array} \right]$$

where R is hydrogen or methyl, and which contains a total of not less than seven aliphatic double bonds, in the essential absence of moisture and of oxygen, with from 0.03 to 0.9 mole percent, based on carotenoid employed, of a strong Lewis acid having a $pk_a$ of from $-10$ to $+4$ or of an alkali metal.

2. A process as claimed in claim 1, wherein the Lewis acid used for said treatment is $AsF_5$, $SbF_5$, $HClO_4$, trifluoroacetic acid, $FSO_3H$, $AgClO_4$, $NO^+SbF_6^-$, $NO_2^+SbF_6^-$, $NO^+AsF_6^-$, $NO^+PF_6^-$, $NO_2^+PF_6^-$, $NO^+BF_4^-$, $NO_2^+BF_4^-$, $NO^+ClO_4^-$, $(CF_3)_2SO_4$, 2,4,6-trinitrophenol, 2,4,6-trinitrophenylsulfonic acid or 2,4,6-trinitrophenylcarboxylic acid.

3. A process as claimed in claim 1, wherein the alkali metal used for said treatment is sodium or potassium.

4. A process as carried out in claim 1, 2 or 3 wherein said treatment is carried out under a noble gas.

5. The electrically conductive polyene product obtained by the process of claim 1.

6. The product-by-process as claimed in claim 5 wherein the carotenoid is a compound selected from the group consisting of β-carotene, crocetindial, canthaxanthene, flexirubin dimethyl ester, sarcinaxanthene, sarcinene and rhodoxanthene.

7. The electrically conductive polyene product obtained by the process of claim 1 in which the treatment is carried out under a noble gas.

8. The product-by-process as claimed in claim 7 wherein the carotenoid is a compound selected from the group consisting of β-carotene, crocetindial, canthaxanthene, flexirubin dimethyl ester, sarcinaxanthene, sarcinene and rhodoxanthene.

* * * * *